(12) United States Patent
Song et al.

(10) Patent No.: US 10,857,389 B2
(45) Date of Patent: Dec. 8, 2020

(54) PROTON THERAPY SYSTEM BASED ON COMPACT SUPERCONDUCTING CYCLOTRON

(71) Applicant: HEFEI CAS ION MEDICAL AND TECHNICAL DEVICES CO., LTD, Anhui (CN)

(72) Inventors: Yuntao Song, Anhui (CN); Jinxing Zheng, Anhui (CN); Qingxi Yang, Anhui (CN); Yonghua Chen, Anhui (CN); Hansheng Feng, Anhui (CN); Lu Liu, Anhui (CN); Junjun Li, Anhui (CN); Kaizhong Ding, Anhui (CN); Gen Chen, Anhui (CN); Pengyu Wang, Anhui (CN); Junsong Shen, Anhui (CN); Mingzhun Lei, Anhui (CN); Jianghua Wei, Anhui (CN)

(73) Assignee: HEFEI CAS ION MEDICAL AND TECHNICAL DEVICES CO., LTD, Anhui (CN)

( * ) Notice: Subject to any disclaimer, the term of this patent is extended or adjusted under 35 U.S.C. 154(b) by 0 days.

(21) Appl. No.: 16/824,547

(22) Filed: Mar. 19, 2020

(65) Prior Publication Data
US 2020/0215353 A1    Jul. 9, 2020

Related U.S. Application Data

(63) Continuation of application No. PCT/CN2018/092110, filed on Jun. 21, 2018.

(30) Foreign Application Priority Data

Oct. 12, 2017    (CN) .......................... 2017 1 0948544

(51) Int. Cl.
*A61N 5/10*      (2006.01)
*A61B 6/03*      (2006.01)
(Continued)

(52) U.S. Cl.
CPC ............ *A61N 5/1048* (2013.01); *A61B 6/035* (2013.01); *A61B 6/102* (2013.01); *A61B 6/4085* (2013.01);
(Continued)

(58) Field of Classification Search
CPC .. A61N 5/1047; A61N 5/1048; A61N 5/1081; A61N 2005/1087; A61N 5/1067;
(Continued)

(56) References Cited

U.S. PATENT DOCUMENTS

| 4,870,287 | A | * | 9/1989 | Cole | ......................... | A61N 5/10 |
| | | | | | | 250/492.3 |
| 2009/0032742 | A1 | * | 2/2009 | Kaiser | ...................... | A61N 5/10 |
| | | | | | | 250/503.1 |

(Continued)

FOREIGN PATENT DOCUMENTS

CN      102695544 A     9/2012
CN      107320859 A    11/2017
(Continued)

OTHER PUBLICATIONS

Zheng Jinxing et al.,Research and Development of the Beam Line for SC200 Superconducting Proton Cyclotron. 21st International Conference on Cyclotrons and their Applications(CYC2016),Jan. 31, 2017(Jan. 31, 2017), entire document,and figures.

*Primary Examiner* — Catherine B Kuhlman
(74) *Attorney, Agent, or Firm* — Wayne & Ken, LLC; Tony Hom (57) ABSTRACT

A proton therapy system based on a compact superconducting cyclotron, including: a superconducting cyclotron system, an energy selection system, a beam transport system, a fixed therapy room subsystem and a rotating frame therapy subsystem; a fixed-energy proton beam extracted from a superconducting cyclotron of the superconducting cyclotron
(Continued)

system is adjusted into a continuous and adjustable proton beam of 70 MeV to 200 MeV by the energy selection system, thus realizing a longitudinal adjustment for a proton range during treating a tumor, and the continuous and adjustable proton beam is respectively transmitted to the fixed therapy room subsystem and the rotating frame therapy subsystem by the beam transport system. The cooperative control of the superconducting cyclotron system, the energy selection system, the beam transport system and the therapy head realizes the transverse expansion of proton beams, thus realizing intensity modulated radiation therapy for the tumor.

4 Claims, 6 Drawing Sheets

(51) Int. Cl.
    *A61B 6/10*     (2006.01)
    *A61B 6/00*     (2006.01)
    *H05H 13/04*     (2006.01)
    *H05H 13/00*     (2006.01)
    *H05H 7/00*     (2006.01)

(52) U.S. Cl.
    CPC ......... *A61N 5/1047* (2013.01); *A61N 5/1067* (2013.01); *A61N 5/1079* (2013.01); *A61N 5/1081* (2013.01); *H05H 13/005* (2013.01); *H05H 13/04* (2013.01); *A61N 2005/1087* (2013.01); *A61N 2005/1095* (2013.01); *H05H 2007/004* (2013.01); *H05H 2277/11* (2013.01)

(58) Field of Classification Search
    CPC ...... A61N 5/1079; A61B 6/102; H05H 13/04; H05H 13/005; H05H 2007/004
    See application file for complete search history.

(56) References Cited

U.S. PATENT DOCUMENTS

2009/0314969 A1    12/2009   Rietzel
2011/0006214 A1*   1/2011   Bonig ..................... H05H 7/18
                                                                      250/396 R

FOREIGN PATENT DOCUMENTS

CN          107596579 A     1/2018
WO         2012033453 A1    3/2012

* cited by examiner

PROTON THERAPY SYSTEM BASED ON COMPACT SUPERCONDUCTING CYCLOTRON

CROSS-REFERENCE TO RELATED APPLICATIONS

This application is a continuation of International Application No. PCT/CN2018/092110 with a filing date of Jun. 21, 2018, designating the United states, now pending, and further claims to the benefit of priority from Chinese Patent Application No. 201710948544.4, filed on Oct. 12, 2017. The content of the aforementioned application, including any intervening amendments thereto, is incorporated herein by reference in its entirety.

TECHNICAL FIELD

The present application relates to medical equipment, and more particularly to a proton therapy system based on a compact superconducting cyclotron.

BACKGROUND

With the increasing demand for cancer therapy, proton therapy has become an effective mean to cure tumors. Proton therapy has a unique "Bragg peak" biological effect. The dose loss is minimal on the track before reaching a target area. The most energy of protons can be released at a predetermined depth, forming an energy releasing track called "Bragg peak" which can accurately cure a tumor area and effectively kill lesions, reduce the damage to surrounding healthy tissues, greatly reduce the damage to normal cells, improve the comfort of patients during therapy, and improve the quality of life of patients after surgery. Compared with the conventional radiotherapy, the proton therapy has a wide therapeutic range, a high cure rate and a high survival rate, a 60% reduction in radiation dose to normal tissues, a shorter time for treating malignant tumors, and an effective reduction in the risk of radiation injury to healthy tissues.

Although the superiority of proton therapy has been widely recognized in the world, the proton therapy system currently used in China is mainly imported from abroad, and the core technology thereof mainly relies on foreign countries, which has a high procurement, high maintenance cost, a large size and a high construction cost, resulting in the extremely high cost of the proton therapy, and most patients cannot afford proton therapy. Therefore, to reduce the procurement, maintenance and construction cost, it is necessary to master the core technology of the proton therapy system, reduce the dependence on borrowing technologies, and improve the layout of the proton therapy system and realize the compactness of the therapy equipment, thereby reducing the cost of the proton therapy.

Chinese Patent Application No. 201480022491.8 discloses an on-board compact proton therapy system with energy selection on a rotatable frame As shown in the accompanying drawings, according to the adaptation of the prior art, a configuration of a medical facility with a proton emission system is provided and is designed to provide a proton beam for a plurality of therapy tables, and an exemplary configuration of a medical facility arranged with a single room proton therapy system is provided.

Chinese Patent Application No. 201610616075.1 provides a cyclotron-based proton therapy system, comprising: a proton cyclotron and a main proton beam transport system for transporting protons in the proton cyclotron. The main proton beam transport system transmits the protons of the required energy to therapy rooms of three different tracks through the switch magnets respectively. The therapy rooms on the three different tracks are a first therapy room on the rotating frame, a second therapy room with horizontal and vertical fixed beams and a third therapy room with horizontal and tilted fixed beams, and the second and third therapy rooms are respectively arranged at two sides of the first therapy room.

Chinese Patent Application No. 201610617089.5 provides a proton therapy system with double fixed rooms and double irradiation beams arranged in dislocation, comprising: a proton cyclotron, a proton beam transport system, and a therapy room with double fixed beams.

The above disclosed techniques mainly have the disadvantages of a large volume, large floor space and no radiation protection for personnel and environment. Moreover, these techniques are required to have a precise identification for tumor patients, an improved preparation time and therapy efficiency.

SUMMARY

To solve problems of that the current proton therapy system has a large area and a high cost, and main core components of the current proton therapy system are still dependent on foreign technology, the invention provides a proton therapy system based on a compact superconducting cyclotron.

The object of the invention can be achieved by the following technical solutions.

A proton therapy system based on a compact superconducting cyclotron, comprising: a superconducting cyclotron system, an energy selection system, a beam transport system, a fixed therapy room subsystem and a rotating frame therapy subsystem; a fixed-energy proton beam extracted from a superconducting cyclotron of the superconducting cyclotron system is adjusted into a continuous and adjustable proton beam of 70 MeV to 200 MeV by the energy selection system, realizing a longitudinal adjustment for a proton range during treating a tumor, and the continuous and adjustable proton beam is respectively transmitted to the fixed therapy room subsystem and the rotating frame therapy subsystem respectively by the beam transport system; the cooperative control of the superconducting cyclotron system, the energy selection system, the beam transport system and the therapy head realize the transverse expansion of proton beam, thus realizing the intensity modulated radiation therapy for the tumor.

The superconducting cyclotron comprises a superconducting magnet system, a high frequency system, an ion source system, a central area, a lead-out area, a magnet unit and a diagnostic unit.

The superconducting magnet system comprises a strong magnetic field superconducting magnet, a superconducting coil terminal box, and a superconducting magnet adjusting structure; the strong magnetic field superconducting magnet is circumferentially arranged on the periphery of the resonant cavity to provide a magnetic field for proton acceleration, and the superconducting coil terminal box is connected with the superconducting magnet to provide a low temperature environment required for the operation of the superconducting magnet; the superconducting magnet adjusting structure comprises twelve adjusting rods which are uniformly arranged on the upper and lower surfaces and the circumferential side of the superconducting magnet respectively, which can adjust the plane position of the coil of the superconducting magnet system.

The high frequency system comprises a high frequency resonant cavity and a tuning rod for the high frequency resonant cavity. The high-frequency resonant cavity has a centrally symmetric spiral fan shape, and is disposed between the two adjacent magnetic poles to provide an accelerating voltage to particles; the tuning rods for the high frequency resonant cavity are symmetrically arranged on the upper surface and the lower surface of the high-frequency resonant cavity respectively; two tuning rods for the high frequency resonant cavity are arranged on the upper and lower surfaces of the high-frequency resonant cavity for fine-tuning the resonant frequency of the high frequency system.

The ion source system comprises a hot cathode ion source, an ion source support and a guide rail. The hot cathode ion source penetrates into the central area along the central axis of the iron yoke under the superconducting cyclotron, and the hot cathode ion source is guided and fixed by the ion source support and the guide rail to provide accelerated particles for the superconducting cyclotron.

The central area is a central area with an adjustable current intensity which comprises a plurality of DEE plates, a plurality of fake DEEs, a plurality of vertical baffles, a plurality of deflection electrodes, a vertical electrode columns, and an ion source; the central area is configured to extract particles from the internal ion source, select and accelerate some particles with ideal motion state, and adjust the current intensity of the beams in the central area as required; the central area is simple in structure and convenient for controlling.

The lead-out area comprises an adjustable beam deflection mechanism and a magnetic channel system; the adjustable beam deflection mechanism includes a radial adjusting mechanism, a support mechanism, an electrostatic deflection plate body and a vacuum high-voltage feeding mechanism; the radial adjustment mechanism comprises a fixed base, a lead screw and a movable block; the support mechanism comprises a mounting plate and a middle pillar; the electrostatic deflection plate body comprises a housing, a high voltage electrode and a cutting plate; the vacuum high-voltage feeding mechanism comprises a high voltage cable, a ceramic insulating sleeve, an elastic conductive terminal, a conductive pin. The magnetic channel system includes MC1, MC2, MC3, and MC4; the magnet unit includes a magnet yoke, a lift cylinder and a magnetic pole; the magnet yoke includes an upper iron yoke cover, an upper iron yoke waist, and a lower iron yoke waist and a lower iron yoke cover, the diagnostic unit comprises a beam diagnostic mechanism of the central area, a beam diagnostic mechanism of the acceleration area, a beam diagnostic mechanism of the lead-out area, and a beam diagnostic mechanism of the lead-out reference point.

The central area with an adjustable current intensity can select and accelerate some particles in more ideal motion state and adjust the beam in the central area as needed. The adjustable beam deflection mechanism enables an electrostatic deflection plate body to achieve overall radial movement to meet the requirement of beam adjustment.

The lead-out area provides an adjustable beam deflection mechanism and a magnetic channel system. The adjustable beam deflection mechanism can deflect the beam from the orbit of the superconducting cyclotron. A magnetic field is generated by the magnetic channel system, and the magnetic field is used to act on protons and angularly deflect the protons until the protons are extracted.

The diagnostic unit of the invention can measure the beam about positions and current intensity at a central area, an acceleration area, a lead-out area, and a lead-out reference point; the diagnostic unit can absorb and block the beam at an end of the lead-out end of the beam.

The proton beam energy which is derived from the superconducting cyclotron system is 200 MeV, and the beam energy needs to be adjusted by the energy selection system according to the therapy depth to achieve the range adjustment thereof in the therapy of tumor.

The energy selection system comprises a graphite reducer, a collimator and a selection slit which have various thicknesses, and the energy selection system also comprises a beam detection device for corresponding various magnets and beam blockers required for particle optics. When protons pass through a graphite layer, the larger the thickness of graphite, the greater the energy reduction, and different thickness of graphite means that the different reduction of the energy can be obtained. When the beams with a 200 MeV fixed energy extracted from the superconducting cyclotron enter into the energy selection system, by adjusting the different thickness of the energy reducer, the various continuous and adjustable energy proton beams of 70 MeV to 200 MeV can be obtained and sent to the therapy head. In addition, the incident proton beam scatters when passing through the energy reducer, resulting in a discrete distribution of beam energy, spatial position, and direction of motion. The distribution of energy is a energy spread, and the distribution of spatial position and direction of motion is a emittance. When a particle passes through the material, the nuclear reaction may occur and a secondary particle is produced, resulting in a certain particle loss and radiation, so a certain radiation shielding measure needs to be considered. In order to ensure the output proton beam meets the required energy spread and the required emittance, the energy selection system has corresponding beam optics which is a collimation device such as a collimator and a selection slit; the energy reducer is configured to reduce beam energy and obtain a beam of energy required for therapy; The beam after passing from the energy reducer is scattered due to scattering, and the property of the beam is controlled within an acceptable range by means of physical restriction of the collimator; The selection slit is used for protons to have energy dispersion when protons pass through the energy reducer. When particles with various energy deflect through the dipole magnet, the beam envelope radius increases in the horizontal direction. By the mean of limiting the selection slit physically, the particles with excessive deviation from the required energy are screened; the beam detection device uses a method of multiwire ionization chamber and a equipment for measuring the center position, current intensity and an emittance of the beam, and a signal is fed back to the correction magnet in the transport line to keep the beam position accurate.

The beam transport system is used for transmitting and controlling the proton beam, and after the proton beam passing through the energy connection selection system, the deflection combination of unique 63-degree and 30-degree dipole iron is used to form a compact transmission line magnet layout. The proton beams with the required energy are transmitted to the therapy subsystems in two different tracks, and one track of the continuous and adjustable proton beam is transmitted to the fixed therapy room subsystem; and the other of the continuous and adjustable proton beam is transmitted to the rotating frame therapy subsystem. a transmission track of the proton beam is provided with a dipole iron, a quadrupole iron and a correction magnet which are used for deflecting, focusing and orbit correcting of the proton beam; the beam blocker is an important component of a beam transport line safety system and is provided with a management sensor with a dedicated actuator such as a limit switch, which monitors an operation status of a executive component of a beam blocker in real time; when receiving an input signal of an abnormal beam, the upper control system can make a timely response and quickly disconnect the beam by mechanical method.

The dipole iron and quadrupole iron of the beam transport system mainly switch various field strengths according to proton beams with various energy to realize the deflection and aggregation of the beam, where the field strength and uniformity of the physical parameters are the key to beam transmission. The dipole iron includes a dipole iron power source for powering the dipole iron; the quadrupole iron includes a quadrupole iron power source for powering the quadrupole iron; the dipole iron power supply and the quadrupole iron power supply are required by the transport line control system to adjust the output current of the power supply according to the therapy demand of the therapy end; the power supply current excites coils of the dipole iron and the quadrupole iron, and a excitation magnetic field is generated by the coils thereof, a iron core increases the field strength and improves the uniformity distribution of the magnetic field in the field, so that the dipole and quadrupole irons generate a dipole field and a quadrupole gradient field respectively; when a proton beam passes through a good field region, the dipole magnetic field and the quadrupole magnetic field are subjected to the Lorentz force, thereby respectively producing an deflection effect and focusing effect; according to the control needs of the therapy end, in the process of rapidly switching of proton beam energy, the corresponding bipolar power supply and quadrupole power supply need to respond quickly to realize the rapid switching of output current; after the excitation current of is switched, the field strength of the two-pole iron and quadrupole magnetic field is also fast switching to meet the requirements of various proton beam energy.

The rotating frame therapy subsystem includes a rotation therapy system, a patient positioning system, a positioning control device, an imaging control device, and a therapy information display system; the rotary therapy system includes a rotary therapy head and an imaging device; the patient positioning system includes a flexible manipulator and a carbon fiber bed; the rotating therapy head can accurately radiate the energy in the beam transport system to a tumor area of a patient by the control system; the imaging device can feedback the tumor information of the patient to the therapy system in real time, and the therapy system adjusts the dose and position of the therapy in real time; the patient positioning system can accurately transport the patient to a therapy site; the carbon fiber bed can achieve ultra-low loss penetration of high energy radiation and control the therapy process with maximum precision. When the proton therapy system of the invention works, a tumor patient lies on a carbon fiber bed, and a patient positioning system composed of a flexible manipulator and a carbon fiber bed accurately transports the patient to the therapy area. a doctor accurately positions the patient's tumor by the imaging system. The required dose is uniformly injected around the tumor by a 360-degree rotating therapy head, greatly reducing the damage to normal tissues. After the patient is treated, the patient positioning system can transport the patient from the therapy posture to the docking posture, so that the patient can easily get on and off the bed.

The invention has the beneficial effects: the beam intensity of the superconducting cyclotron of the invention can be adjusted, and the intensity-modulating therapy can be realized; the compact built-in ion source reduces the volume and the cost of the superconducting cyclotron; the compact floor space reduces structural costs and improves service performance; there is no high energy consumption and high heat dissipation caused by the constant temperature electromagnet; by reasonably designing the geometry of the DEE plate and the fake DEE in the acceleration area, the beam can meet the requirements such as non-slip phase and fast centralization; the superconducting cyclotron of the invention can screen out an ideal particle in the moving state, improve the beam quality, adjust the current intensity as required, thus the superconducting cyclotron is simple in structure and convenient for controlling; the superconducting cyclotron of the invention can realize the overall radial movement of the electrostatic deflection plate body according to the beam adjustment, which is convenient and flexible; the superconducting cyclotron of the invention uses a beam load at the end of the beam outgoing end to absorb and block the beam to avoid radiation damage to personnel and the environment.

The beam with fixed energy of 200 MeV which is extracted by the superconducting cyclotron of the invention enters the energy selection system, and by continuously adjusting various thicknesses of an energy reducer, a continuous and adjustable proton beam from 70 MeV to 200 MeV can be realized; the beam transport system uses a unique 63-degree 30-degree dipole iron deflection combination to form a magnet layout of a compact transmission line; the rotating frame main body uses a variable diameter cylindrical coil structure, and the overall structure of the rotating frame main body is compact; the rotating frame drive structure comprises dual driving gears and a single driven gear, and uses the position full-closed loop control system can realize high-precision rotary positioning; the rotating frame safety control system uses a multi-directional detection method, and corresponding position signal feedback devices are arranged at a key equipment such as a therapy head and a CBCT device to ensure the safety and reliability of the overall operation of the superconducting cyclotron.

The rotating frame therapy subsystem of the invention can quickly locate the tumor patient through the combined action of a flexible manipulator, a carbon fiber therapy bed and an imaging system, thus greatly reducing the therapy preparation time and improving the therapy efficiency; after initial positioning of the patient through the patient positioning system, the imaging device is directly used to image the patient's tumor, and the imaging result is fed back to the therapy system, and the therapy system can directly and accurately locate and treat patients according to the imaging result, thereby avoiding the problem of inaccurate therapy caused by a secondary localization of traditional patient imaging and therapy separation and greatly improving the precision of tumor therapy; by rotating the therapy head, the dose required for tumor therapy is uniformly injected into a body from the skin around the tumor, and the dose is dispersed to avoid the huge damage to normal tissue cells caused by the concentration of radiation in the conventional radiotherapy, thus reducing the side effects caused by therapy and greatly improving the quality of life of patients after surgery.

The invention is innovative and practical and can effectively solve the problems such as inaccurate tumor positioning in current tumor therapy, long therapy process, and poor postoperative quality of life of patients after surgery; the invention plays an extremely important role in promoting the precision, effectiveness and efficiency of tumor therapy for patients.

BRIEF DESCRIPTION OF THE DRAWINGS

The invention is further described below with reference to the accompanying drawings, from which those skilled in the art can better understand the invention.

In the drawings: 10, superconducting cyclotron; 11, fixed therapy room subsystem; 12, rotating frame therapy subsystem; 101, central area; 1011, DEE plate; 1012, fake DEE; 1014, vertical electrode column; 1015, vertical baffle; 1016, deflection electrode; 102, magnet unit; 1021, upper iron yoke cover; 1022, upper iron yoke waist; 1023, lower iron yoke waist; 1024, lower iron yoke cover; 1025, lift cylinder; 1026, magnetic pole; 103, adjustable beam deflection mechanism; 1031, radial adjustment mechanism; 10311, fixed base; 10312, lead screw; 10313, movable block; 1032, support mechanism; 10321, mounting plate; 10322, middle pillar; 1033, electrostatic deflection plate body; 10331, housing; 10332, high voltage electrode; 10333, cutting plate; 1034, vacuum high-voltage feeding mechanism; 104, magnetic channel system; 1041, MC1; 1042, MC2; 1043, MC3; 1044, MC4; 105, diagnostic unit; 1051, beam diagnostic mechanism of central area; 1052, beam diagnostic mechanism of acceleration area; 1053, beam diagnostic mechanism of lead-out area; 1054, beam diagnostic mechanism of lead-out reference point; 1061, high frequency resonant cavity; 1062, tuning rod for the high frequency resonant cavity; 1071, hot cathode ion source; 1072, ion source support and guide rail; 1081, strong magnetic field superconducting magnet; 1082, superconducting coil terminal box; 1083, superconducting magnet adjusting structure; 12101, first focusing quadrupole iron; 12111, second focusing quadrupole iron; 12102, first 63-degree deflection dipole iron; 12103, second 63-degree deflection dipole iron; 12104, first 30-degree deflection dipole iron; 12105, second 30-degree deflection dipole iron; 12106, third 30-degree deflection dipole iron; 12107, fourth 30-degree deflection dipole iron; 12108, first 60-degree deflection dipole iron; 12109, second 60-degree deflection dipole iron; 12110, 90-degree deflection dipole iron; 122, energy reducer; 122, multiwire ionization chamber; 1231, first collimator; 1232, second collimator; 124, restriction slit; 1251, first beam blocker; 1252, second beam blocker; 1253, third beam blocker; 1254, fourth beam blocker; 1255, fifth beam blocker; 1261, first vacuum window; 1262, second vacuum window; 127, rotating frame; 1271, dual driving gear; 1272, single driven gear; 1274, CBCT device; 1281, fixed therapy head; 1282, rotating therapy head; 12901, correction magnet; 12902, phase probe; 1312, flat plate receiver; 1313, imaging bulb tube; 1314, flexible manipulator; 1315, carbon fiber therapy bed; 1316, movable handle; 1317, therapy information display system; 1318, imaging control device.

DETAILED DESCRIPTION OF EMBODIMENTS

The invention is described in the following with reference to the embodiments of the invention, from which technical solutions of the invention will become more clear and complete. Apparently, embodiments described herein are only parts of the invention. Based on the embodiments of the invention, all other embodiments obtained by those skilled in the art without making creative efforts shall fall within the scope of the invention.

Figure 1:
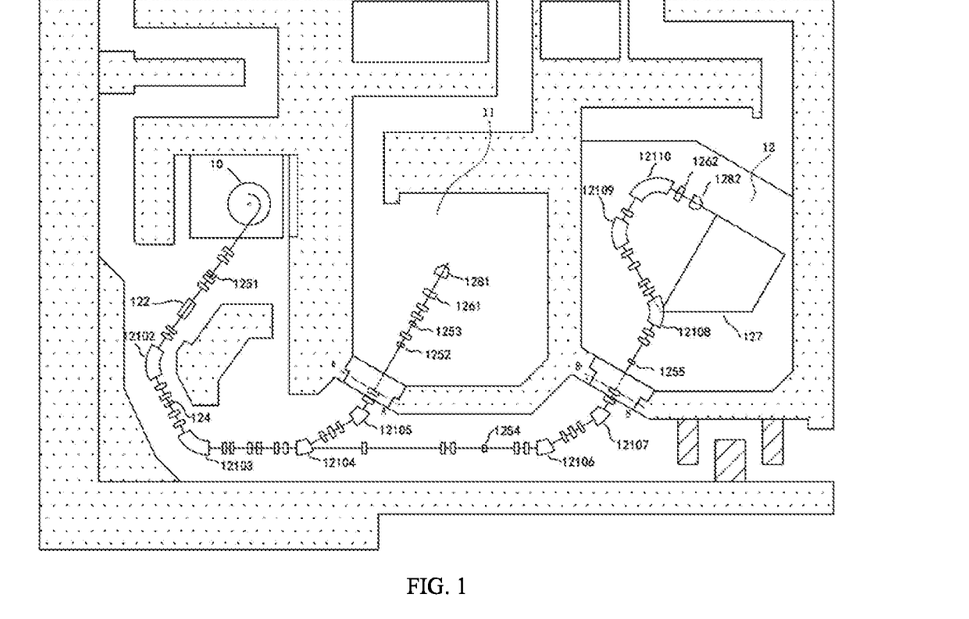
FIG. 1 is a schematic layout view of a medical facility of a proton radiation system with dual rooms.

The invention provides a proton therapy system based on a compact superconducting cyclotron, comprising: a superconducting cyclotron system, an energy selection system, a beam transport system, a fixed therapy room subsystem 11 and a rotating frame therapy subsystem 12; where in the superconducting cyclotron system, proton beams are extracted by a superconducting cyclotron 10, and then reaches the fixed therapy room subsystem 11 and the rotating frame therapy subsystem 12 respectively through the energy selection system and the beam transport system.

Specifically, in FIG. 1, a fixed-energy proton beam extracted from a superconducting cyclotron 10 is adjusted into a continuous and adjustable proton beam of 70 MeV to 200 MeV by an energy reducer 122, thus realizing a longitudinal adjustment for a proton range during treating a tumor; then the continuous and adjustable proton beam passes a first 63-degree deflection dipole iron 12102 and a restriction slit 124 to adjust an emittance of the continuous and adjustable proton beam; the continuous and adjustable proton beam with the required energy passes are respectively transmitted to therapy subsystems of two different tracks by passing a second 63-degree deflection dipole iron 12103 and a first 30-degree deflection dipole iron 12104; one track of the continuous and adjustable proton beam is transmitted to the fixed therapy room subsystem 11 by passing through a second 30-degree deflection diode 12105, and the other track of the continuous and adjustable proton beam is transmitted to the rotating frame therapy subsystem 12 by passing through a third 30-degree deflection dipole iron 12106 and a fourth 30 degree deflection dipole iron 12107, and then to a rotating therapy head 1282 by passing a first 60-degree deflection dipole iron 12108, a second 60-degree deflection dipole iron 12109, a 90-degree deflection dipole iron 12110. The continuous and adjustable proton beam is transmitted in vacuum between an outlet of the superconducting cyclotron 10 and a first vacuum window 1261 of the fixed therapy room subsystem 11, and the continuous and adjustable proton beam performs tumor radiotherapy through a fixed therapy head 1281; the continuous and adjustable proton beam is transmitted in vacuum between the outlet of the superconducting cyclotron 10 and the second vacuum window 1262 of the rotating frame therapy subsystem 12, and the continuous and adjustable proton beam performs tumor radiotherapy through a rotating therapy head 1282.

A first beam blocker 1251 is arranged at the outlet of the superconducting cyclotron 10. When an accident happens, the first beam blocker 1251 is immediately started to block the beam from being transmitted to the transport line, which is only used as a secondary safety guarantee for stopping the beam source; to ensure the absolute safety, the fixed therapy room subsystem 11 is provided with a second beam blocker 1252 and a third beam blocker 1253, and both the second beam blocker 1252 and the third beam blocker 1253 are provided inside the fixed therapy room subsystem 11; the rotating frame therapy subsystem 12 is provided with a fourth beam blocker 1254 and a fifth beam blocker 1255; the fourth beam blocker 1254 is arranged outside the rotating frame therapy subsystem 12, and the fifth beam blocker 1255 is arranged inside the rotating frame therapy subsystem 12. Performing multiple cut-off protection in case of failure and preventing the beam from entering during therapy section maintenance guarantee that patients will not receive the wrong dose of harm during therapy or other workers will not receive the wrong dose of injury while working.

Figure 2:
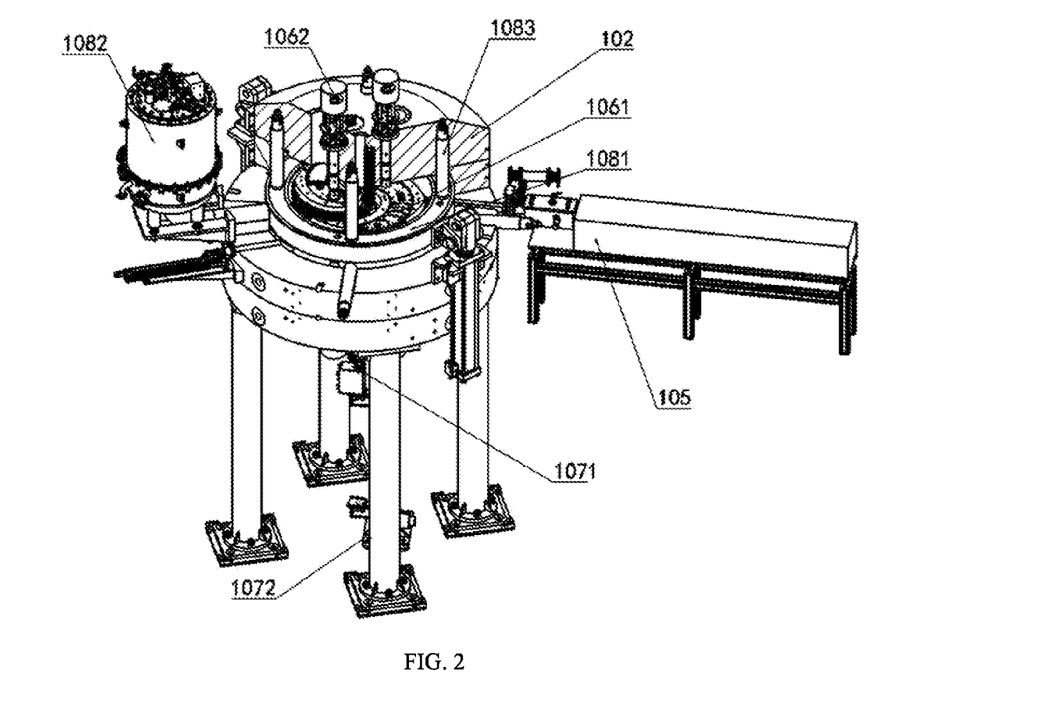
FIG. 2 is a schematic view of a superconducting cyclotron of the present invention.

As shown in FIG. 2, it is a schematic view of the superconducting cyclotron 10 of the invention. The superconducting cyclotron 10 mainly consists of a superconducting magnet system, a low temperature system, a high frequency system, an ion source system, a central area, a lead-out area, a magnet unit and a diagnostic unit. The central area is configured to extract particles from the internal ion source, accelerate some particles with an ideal motion state, and adjust the intensity of the central beam as required. In the lead-out area, the beam accelerated to a predetermined energy is deflected and directed out of the accelerator, so as to transmit the beam to respective terminals, thus ensuring the highest extraction efficiency and the best quality of the extracted beam. The function of the magnet unit is to generate a suitable magnetic field to restrain the particles to rotate outwards and ensure that the rotating frequency of the particles meets the isochronous requirements; the beam is focused horizontally, and the working point of the beam is away from harmful resonance, or the beam quickly passes through the resonance band. The diagnostic unit is used to measure information such as the position and intensity of the beam.

The superconducting magnet system comprises a strong magnetic field superconducting magnet 1081, a superconducting coil terminal box 1082, and a superconducting magnet adjusting structure 1083; the strong magnetic field superconducting magnet 1081 is circumferentially arranged on the periphery of the resonant cavity to provide a magnetic field for proton acceleration, and the superconducting magnet coil terminal box 1082 is connected with the strong magnetic field superconducting magnet 1081 to provide a low temperature environment required for the operation of the superconducting magnet; the superconducting magnet adjusting structure 1083 comprises twelve adjusting rods which are uniformly arranged on the upper and lower surfaces and the circumferential side of the superconducting magnet respectively, to adjust the plane position of a coil.

The high frequency system comprises a high-frequency resonant cavity 1061 and a tuning rod for the high frequency resonant cavity 1062. The high-frequency resonant cavity 1061 has a centrally symmetric spiral fan shape, and is disposed between the magnetic poles to provide an accelerating voltage to the particles; the tuning rods for the high frequency resonant cavity 1062 are symmetrically arranged on the upper surface and the lower surface of the high-frequency resonant cavity 1061; two tuning rods are arranged on the upper and lower surfaces of the high-frequency resonant cavity for fine-tuning the resonant frequency of the high frequency system.

The ion source system comprises a hot cathode ion source 1071, an ion source support and guide rail 1072. The hot cathode ion source 1071 penetrates the central area along the central axis of the iron yoke under the superconducting cyclotron, and the hot cathode ion source is guided and fixed by the ion source support and guide rail 1072 to provide accelerated particles for the superconducting cyclotron 10.

Figure 3:
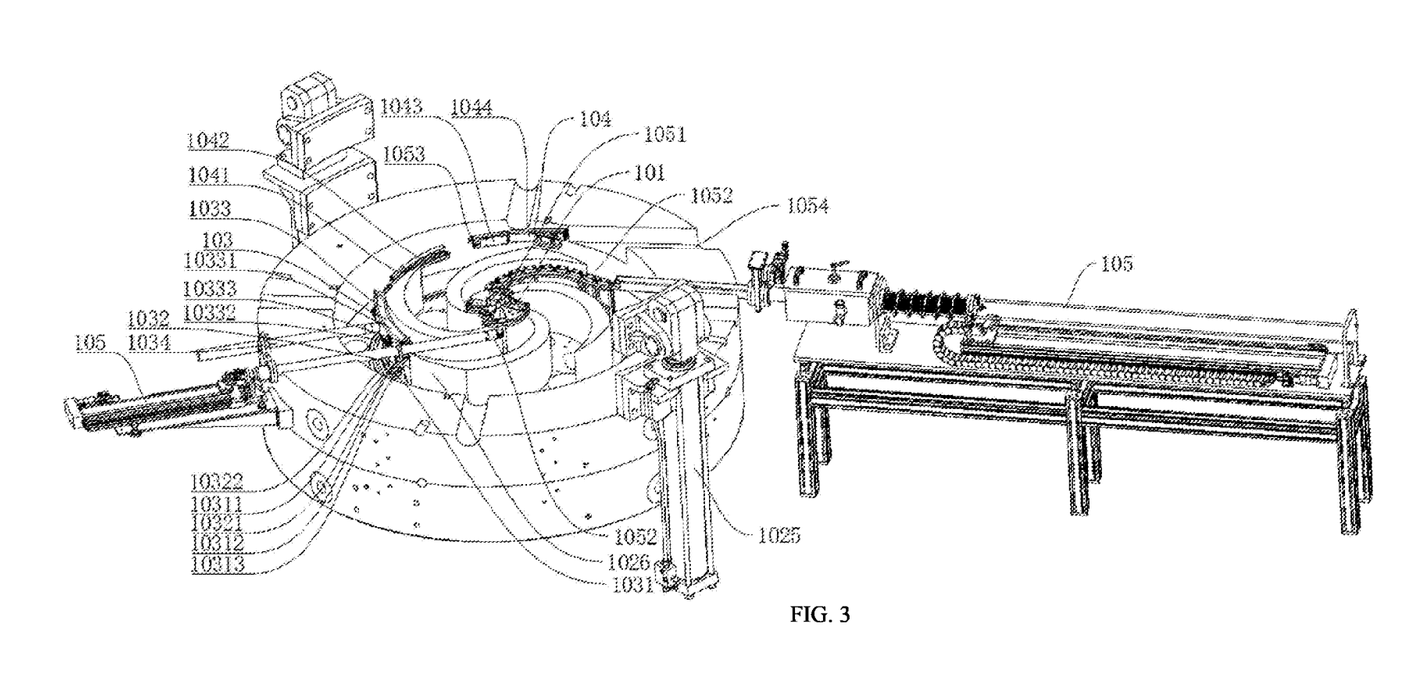
FIG. 3 is a partial enlarged view of a superconducting cyclotron of the present invention.
Figure 4:
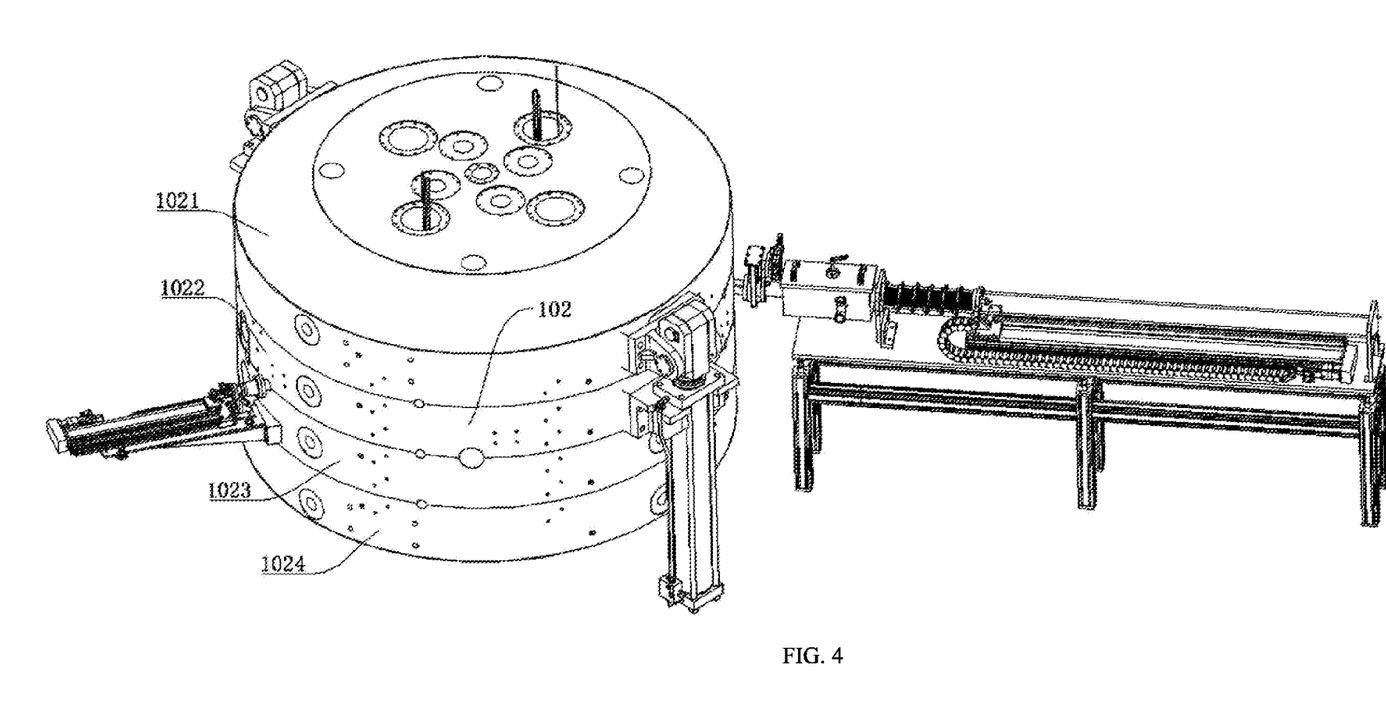
FIG. 4 is a schematic view of a magnet unit of the superconducting cyclotron.
Figure 5:
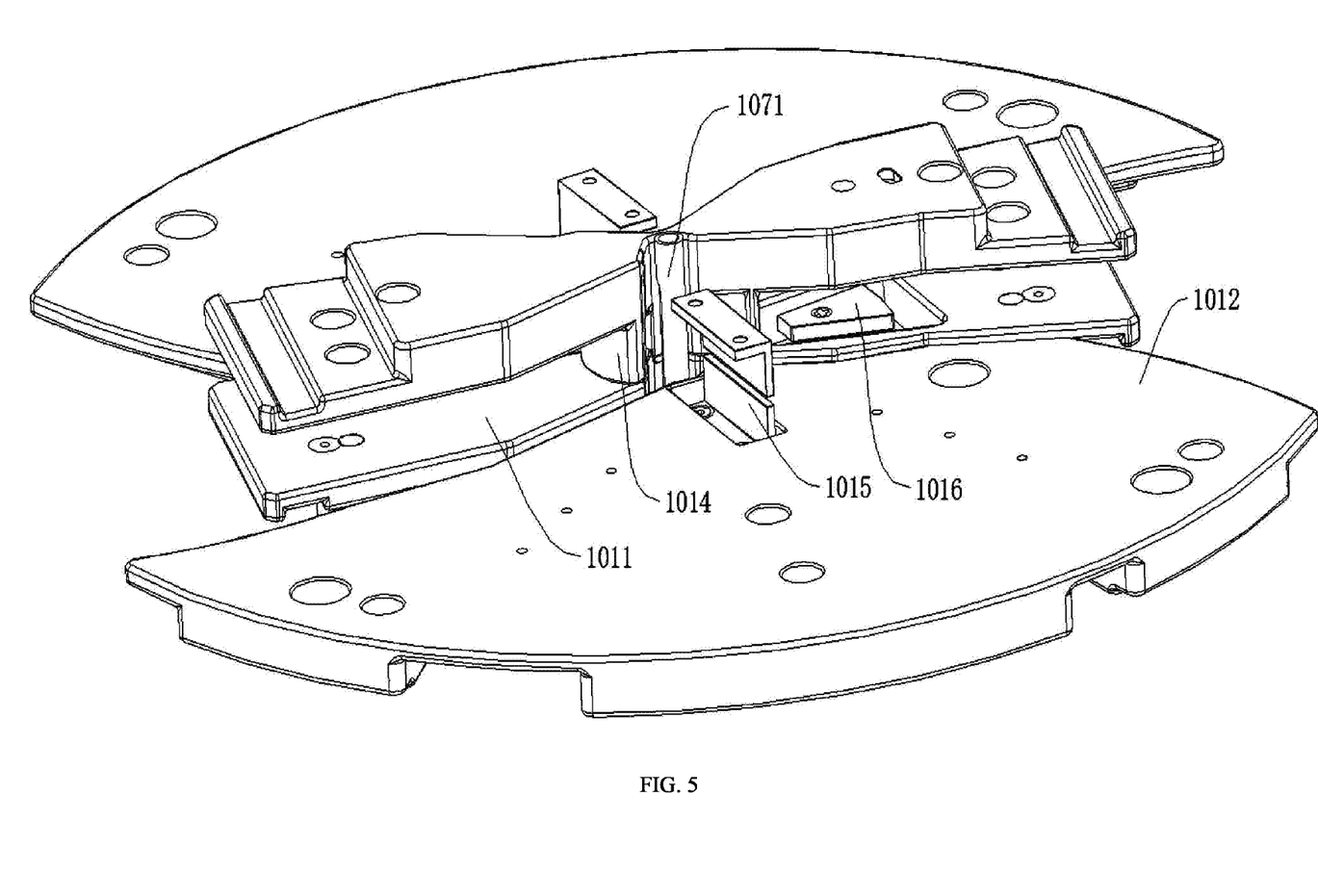
FIG. 5 is a schematic view of an acceleration area of the superconducting cyclotron.

As shown in FIGS. 3-5, the superconducting cyclotron 10 comprises a central area 101 and a lead-out area, a magnet unit 102 and a diagnostic unit 105. The lead-out area comprises an adjustable beam deflection mechanism 103 and a magnetic channel system 104. The central area is a central area with an adjustable current intensity and comprises a plurality of DEE plates 1011, a plurality of fake DEEs 1012, a plurality of vertical baffles 1015, a plurality of deflection electrodes 1016, and a vertical electrode column 1014. The adjustable beam deflection mechanism 103 is configured to deflect and extract the beam; the adjustable beam deflection mechanism 103 comprises a radial adjusting mechanism 1031, an electrostatic deflection plate body 1033, a support mechanism 1032 for supporting the electrostatic deflection plate body 1033, and a vacuum high-voltage feeding mechanism 1034 for feeding the high voltages into the electrostatic deflection plate body 1033. The radial adjustment mechanism 1031 includes a fixed base 10311, a lead screw 10312, and a movable block 10313. The support mechanism 1032 includes a mounting plate 10321 and a middle pillar 10322. The electrostatic deflection plate body 1033 comprises a housing 10331, a high voltage electrode 10332 and a cutting plate 10333. The magnetic channel system 104 comprises MC1 1041, MC2 1042, MC3 1043, and MC4 1044. The magnet unit 102 comprises a magnet yoke, a lift cylinder 1025 and a magnetic pole 1026. The magnetic yoke comprises an upper iron yoke cover 1021, an upper iron yoke waist 1022, a lower iron yoke waist 1023 and a lower iron yoke cover 1024. The diagnostic unit 105 comprises a beam diagnostic mechanism of the central area 1051, a beam diagnostic mechanism of the acceleration area 1052, a beam diagnostic mechanism 1053 of the lead-out area, and a beam diagnostic mechanism of the lead-out reference point 1054.

The central area 101 is configured to extract particles from the hot cathode ion source 1071, and select and accelerate some particles with ideal motion state, and adjust the beam intensity of the central area 101 as required.

The central area 101 is provided with six metal plates in three groups which are vertically symmetrical, and the DEE plates 1011 are a middle group of the three groups, and the DEE plates 1011 are connected with a RF cavity of the main acceleration area; two sides groups of the fake DEEs 1012 which are fixed on the magnetic pole 1026, which is equivalent to the grounding and has a zero potential; four acceleration gaps are formed between the DEE plates 1011 and the fake DEEs 1012.

The vertical electrode column 1014 is arranged near a first acceleration gap directly opposite to the hot cathode ion source 1071 and fixed on the DEE plates 1011; the vertical electrode column 1014 is configured to optimize the electric field distribution of the first acceleration gap and shield stray electric fields, which makes particles accelerate more efficiently.

The vertical baffles 1015 are two groups of vertically symmetrical baffles disposed on a first circles of tracks of the particles in a gyration motion and are fixed on the fake DEE 1012; the vertical baffles 1015 is used to block particles with larger axial amplitude, so that particles with better motion are selected, which is conducive to final extraction.

The deflection electrodes 1016 are a vertically symmetrical electrode group disposed on a first circles of tracks of the particles in a vertical direction. The deflection electrodes 1016 are arranged on the DEE plates 1011 through a groove; by applying a voltage to the deflection electrodes 1016, an electric field in a vertical direction is generated to deflect the particles to hit the vertical baffles 1015; the number of particles hitting the vertical baffle 1015 can be changed by changing the voltage of the deflection electrode 1016, thereby achieving the adjustment of the current intensity of the beam. When not working, the deflection electrode 1016 is connected with the DEE plate 1011; and both upper and lower the deflection electrodes 1016 are equipotential to the DEE plates 1011. When the deflection electrodes 1016 are working, different voltages are applied to the upper and lower deflection electrodes 1016 to generate a deflection electric field. The position and size of the deflection electrode 1016 are adjusted, so that the particles can be completely deflected under the electric field with an intensity of not more than 5 kV/cm to adjust the current intensity of the beam.

The vertical electrode column 1014 generates an electric field which is perpendicular to and outward from an outlet of the hot cathode ion source 1071 to pull the particles out of the hot cathode ion source 1071, and the particles enter the central area 101 for acceleration.

Contour shapes of the DEE plate 1011 and the fake DEE 1012 at the acceleration gap are changed to reasonably design the position and width of the acceleration gap, so that the particles can be accelerated efficiently, thus meeting the requirements of non-slip phase and rapid centralization.

Four superconducting coil rod holes are symmetrically arranged on an upper surface of the upper iron yoke cover 1021 and a lower surface of the lower iron yoke cover 1024 at 90 degrees respectively; four tie rod holes are respectively arranged on the upper iron yoke waist 1022 and the lower iron yoke waist 1023 at 90 degrees; in addition, two probe holes are arranged in the middle plane of the upper iron yoke waist 1022 and the lower iron yoke waist 1023, one of the two probe holes is for the extracting beams, and the other probe hole is for feeding a high voltage to the electrostatic deflection plate.

The adjustable beam deflection mechanism 103 is used to deviate the beam from an orbit of superconducting cyclotron 10, and the cyclotron of superconducting cyclotron 10 which is located in the valley area of the superconducting cyclotron 10 and on the inner surface of the near ring superconducting magnet. The adjustable beam deflection mechanism 103 and the magnetic channel system 104 together form the superconducting cyclotron 10 beam extraction system, which has a great improvement on the efficiency of extracting of the superconducting cyclotron 10.

The radial adjustment mechanism 1031 can make the adjustable beam deflection mechanism 103 realize the overall radial movement according to the needed adjustment of beams. The radial adjustment mechanism 1031 includes a fixed base 10311, a lead screw 10312, and a movable block 10313. The support mechanism 1032 fixedly connects the radial adjustment mechanism 1031 and the electrostatic deflection plate body 1033. The support mechanism 1032 includes an upper-lower mounting plate 10321 and a middle pillar 10322. The support mechanism 1032 is arranged on the movable block 10313 of the radial adjustment mechanism 1031. The lead screw 10312, the movable block 10313 and other components mounted on the radial adjustment mechanism 1031 can realize the overall radial movement relative to the fixed base according to the needed adjustment of beams. The electrostatic deflection plate body 1033 is a component that deflects the beam. The electrostatic deflection plate body 1033 includes a housing 10331, a high voltage electrode 10332, and a cutting plate 10333. The position of the high voltage electrode 10332 is adjustable, an extraction electric field is generated between the high voltage electrode 10332 and the cutting plate 10333. Under the action of the extraction electric field and the magnetic field of the superconducting cyclotron 10, the beam gradually deviates from the orbit in the area of the electrostatic deflection plate body 1033, and then enters the area of the magnetic channel system 104. The vacuum high-voltage feeding mechanism 1034 is a vacuum conductive rod which provides a high-voltage source for the high voltage electrode 10332 with adjustable position of the electrostatic deflection plate. The vacuum high-voltage feeding mechanism 1034 includes a high-voltage cable, a ceramic insulating sleeve, an elastic conductive terminal, and a conductive pin. Due to the different potential between the high voltage electrode 10332 and the electrostatic deflector beam cutting plate 10333, the electric field between the high voltage electrode 10332 and the electrostatic deflector beam cutting plate 10333 produces an electric field force on the beam, which makes the track of the beam deflect.

The magnetic channel system 104 is a key component for extracting protons, and the layout of the magnetic channel system 104 has a great improvement on the extraction efficiency of the superconducting cyclotron 10. The MC1 1041 comprises two iron blocks along the direction of the beam track line. The two iron blocks are symmetrically arranged up and down, and the beam passes through a gap between the two iron blocks. The MC2 1042, MC3 1043, and MC4 1044 respectively consist of three iron blocks arranged along the beam track line. Three iron blocks of the MC2 1042 and three iron blocks of the MC4 1044 are symmetrically and vertically arranged on the outside of the beam, and the iron blocks with a large lateral surface area of MC2 1042 and MC4 1044 are respectively located inside the beam. Three iron blocks of the MC3 1043 are symmetrically and vertically arranged on the inside of the beam, the iron block of the MC3 1043 with a large lateral surface area is located inside the beam.

The beam passes through the middle gap of the three iron blocks MC2 1042, MC3 1043, and MC4 1043; the protons deviate from an angle thereof by passing through the electrostatic deflection plate body 1033, and then sequentially enter the gaps of MC1 1041, MC2 1042, MC3 1043, and MC4 1044. The magnetic channel system 104 uses the magnetic field generated by the magnetic channel system 104 to deflect the protons until the protons are extracted, which affects the intensity of the magnetic field that the beam passes through, thus having a great improvement on the extracting of the beam and the extracting efficiency of the beam.

The beam diagnostic mechanism 1051 of the central area online or offline measures positions of the first circles of the beam of the central area.

The beam diagnostic mechanism 1052 of the acceleration area online measures the axial and radial positions and flow intensity information of the beam at different radii of the acceleration area; In order to accurately measure the beam motion trace, probes are arranged in multiple valleys of the superconducting cyclotron 10 for simultaneous multipoint measurement.

The beam diagnostic mechanism 1053 of the lead-out area online or offline measures the beam positions of the electrostatic deflection plate body 1033 at the lead-out area and the axial and radial beam positions of an outlet and inlet positions of the magnetic channel system 104;

The beam diagnostic mechanism 1054 of the lead-out reference point online measures a position, profile, current intensity and phase of the beam exiting a lead-out end of the superconducting cyclotron 10, with a distance of 1.8 meters away from an axis of the superconducting cyclotron, and the phase of the beam is the fundamental frequency of the 10 RF system relative to the superconducting cyclotron. During the acceptance of the superconducting cyclotron 10, a beam load is also used at the end of the beam exit end to absorb and block the beam to avoid radiation damage to personnel and the environment. Since the beam diagnostic mechanism of the lead-out reference point is the finished product, only the position is marked in the schematic diagram, because the structure of the schematic diagram is drawn.

Figure 6:
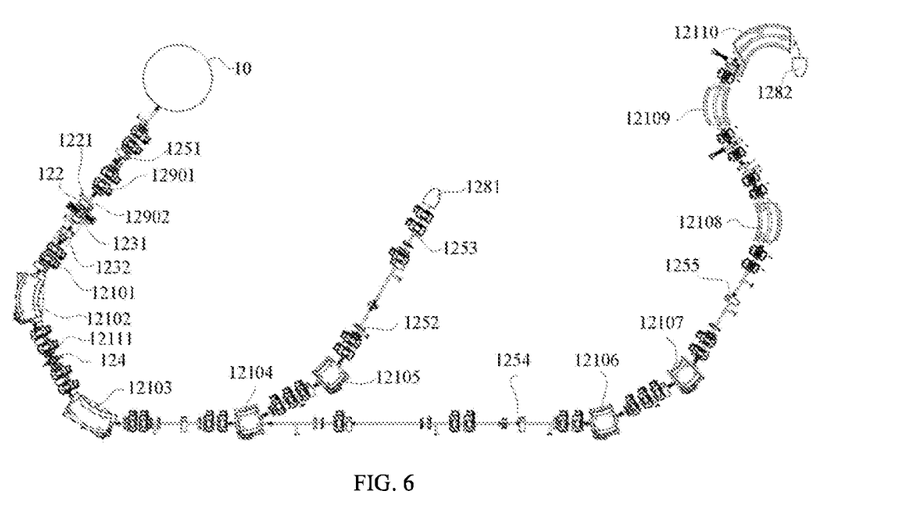
FIG. 6 is a schematic diagram of a beam transport system of a proton radiation system.

In FIG. 6, the fixed energy proton beam is extracted by the superconducting cyclotron 10 and sent to an energy selection and emittance control section to form a double beam waist at an energy reducer 122, so that the reducer 122 works at the best condition; a multiwire ionization chamber 1221 arranged at a front of the energy reducer 122 is used for detecting the position of the proton beam; if the beam position deviates from a center of the superconducting cyclotron 10, after being processed by a control system, a position deviation signal is automatically fed back to a former correction magnet 12901, thus making the beam position be automatically stabilized at a center point; a phase probe 12902 is arranged at the front of the energy reducer 122 to measure the high-frequency phase of the beam extracted for locking and controlling the magnetic field and the high-frequency phase, and a first beam blocker 1251 is arranged at the front of the energy reducer 122 for beam debugging and beam operation safety.

The fixed-energy proton beam is adjusted by the energy reducer 122 to a continuous and adjustable energy according to a thickness of a wedge-shaped graphite block adjusted in the beam direction, however, with the process of energy reduction, the quality of the beam, especially the emittance thereof, increases obviously; In order to ensure that the diverged beam can be reduced to a range less than the reception of the downstream beam transport line before entering the downstream beam transport line, a first collimator 1231 is disposed behind the energy reducer 122 to block the proton beam with a diameter larger than that of the collimation pore thereof and a proton beam with an excessive emissivity.

The proton beam passes through an energy selection and emittance control section to an energy and energy spread control section; two first focusing quadrupole irons 12101 are disposed behind the second collimator 1232 to divert the diverging beam after energy reduction into the first 63-degree deflection dipole iron 12102 for performing deflection; two second focusing quadruples 12111 are disposed at the back of the first 63-degree deflection dipole iron 12102 to stabilize a beam performance at the middle point between the two second focusing quadrupole irons 12111 to form a waist, so that the protons with energy spread deviate from the radial center orbit at the middle point at the maximum deviation from the radial center orbit; the restriction slit 124 is arranged at the middle point, and an absolute energy value for passing the beam is determined by the two first 63-degree deflection dipole iron 12102 as a midpoint of the beam energy passing through a center of the restriction slit 124 to adjust a gap value between a restriction slit, and the purpose of adjusting the emittance of the proton beam can be achieved.

Figure 7:
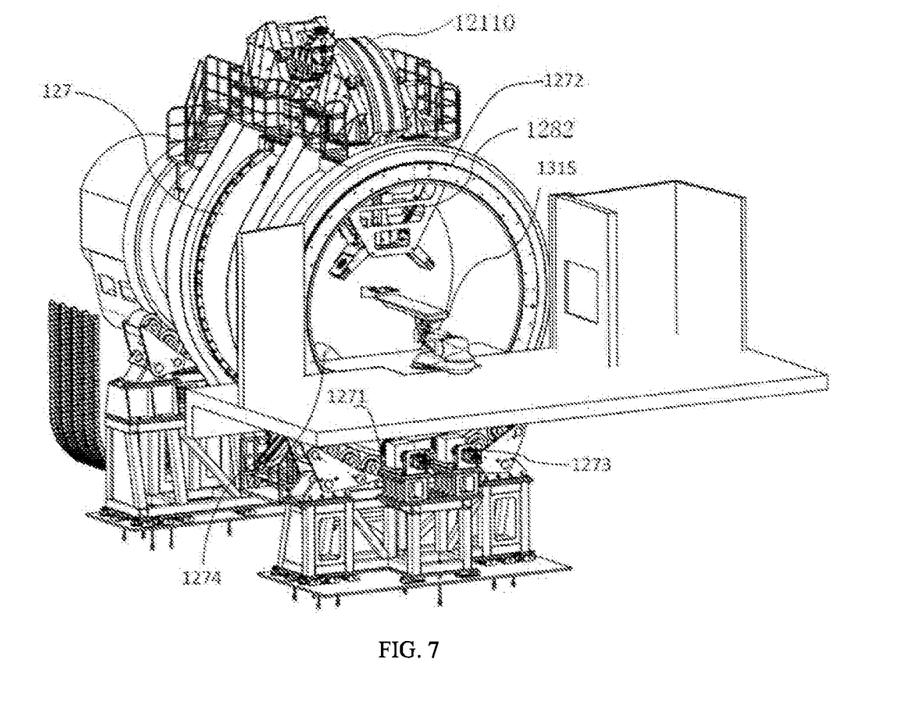
FIG. 7 is a schematic view of a therapy end of the rotating frame.

In FIG. 7, the rotating frame 127 has a cylinder crimping main body structure with a varying diameter, and is designed according to a direction of a beam line of the rotating frame 127 to ensure a compact structure and ensure that a space of the therapy room meets the therapy requirements; a drive system of the rotating frame 127 uses a single driven gear 1272 to match with a dual driving gear 1271, when the rotating frame 127 receives a motion instruction, the motion instruction is transmitted to a position full-closed control system, which drives the dual driving gear 1271, to drive the single driven gear 1272 to achieve precise positioning of the rotating frame 127; the rotating therapy head 1282 and a CBCT device 1274 are fixedly connected with the rotating frame 127; the rotating frame 127 uses a multi-directional detection method, and when the carbon fiber therapy bed 1315 collides with the rotating therapy head 1282 and the CBCT device 1274 during the rotation process of the rotating frame 127, a position encoder 1273 sends out an emergency signal, and the drive system of the rotating frame 127 acts immediately to complete an emergency stop, thus ensuring the safe operation of the rotating therapy head 1282 and the CBCT device 1274.

Figure 8:
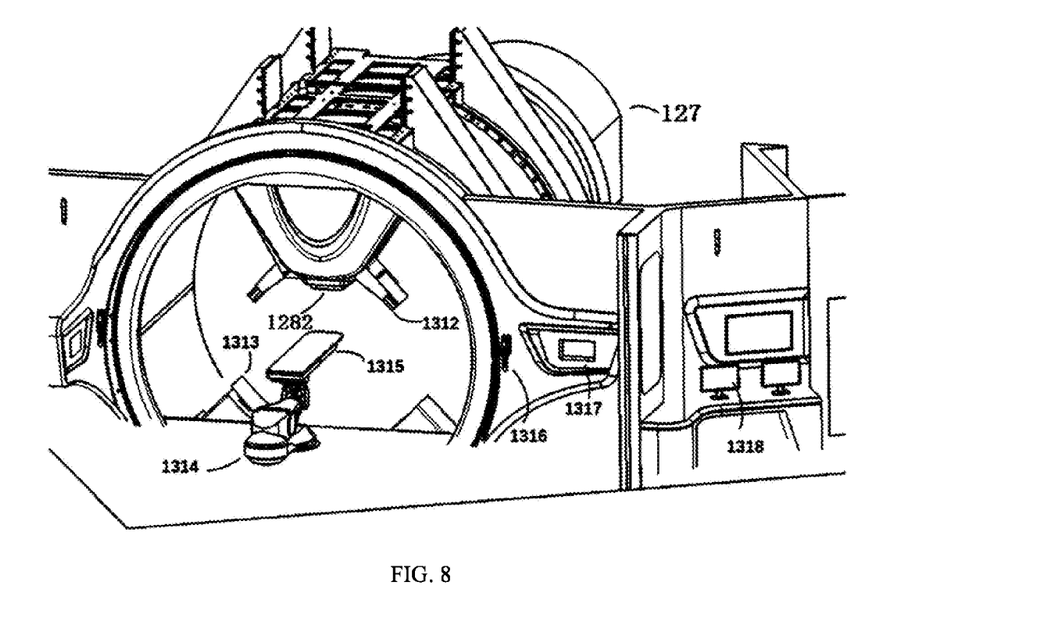
FIG. 8 is a schematic view of a rotating frame therapy subsystem of a proton therapy system.

In FIG. 8, the rotating frame therapy subsystem 12 includes a rotating therapy system located, a patient positioning system, a movable handle, and a therapy information display system 1317. The rotary therapy system is located in a therapy room and includes a rotary therapy head 1282 and an imaging device. The imaging device includes a flat plate receiver 1312, an imaging bulb tube 1313, and an imaging control device 1318. The imaging device 1318 includes an imaging control server, a monitor, and a keyboard. The patient positioning system includes a flexible manipulator 1314 and a carbon fiber therapy bed 1315.

The rotating therapy head 1282 and the flat plate receiver 1312 of the imaging device are mounted on the rotating frame 127. The rotating frame 127 can rotate more than 360 degrees around the therapy center, so that the rotating therapy head 1282 can achieve more than 360 degrees rotation therapy.

The flexible manipulator 1314 is capable of carrying the carbon fiber therapy bed 1315 to perform switching a variety of postures, which can realize rapid and accurate switching of a tumor patient from a docking mode to a specific therapy mode. The carbon fiber therapy bed 1315 can achieve extremely high radiation penetration, so that the rotary therapy head 1282 can perform penetrating therapy on a tumor patient lying on the carbon fiber therapy bed 1315 from the bottom of the carbon fiber therapy bed 1315.

The patient positioning system is controlled by the movable handle, which is convenient for a doctor to operate the patient positioning system from various angles.

The therapy information display system 1317 is located on the wall near the rotating frame 127, and can display various therapy information during the therapy of a patient in real time, which is convenient for a doctor to check. The therapy information display system 1317 is a medical display device to display important therapy information during a therapy process.

The imaging control device 1318 is located in the therapy room away from the rotating frame area, which can maximize the protection of a doctor while imaging a patient's tumor, so that the radiation dose received by the doctor can be controlled within a safe range.

When the proton therapy system of the invention works, the patient positioning system composed of the flexible manipulator 1314 and the carbon fiber therapy bed 1315 is in a docking mode. In this mode, a tumor patient can easily go to bed to lie down and enter the therapy preparation stage. An operator such as a doctor uses the patient positioning system to transport the patient to a initial posture required for therapy through the positioning control device 1316, and operates the imaging bulb tube 1313 and the flat plate receiver 1312 through the imaging control device 1318 to obtain the patient's tumor image and send the patient's tumor image to the therapy system. Some therapy information in this process is displayed by the therapy information display system 1317. The therapy system accurately positions the patient according to the impact of the tumor. The therapy system controls the rotating therapy head 1282 to adjust the intensity of the patient's tumor.

A fixed-energy proton beam stream extracted from a superconducting cyclotron 10 of the superconducting cyclotron system in the invention is used to adjusted into a continuous and adjustable proton beam of 70 MeV to 200 MeV by the energy selection system, thus realizing a longitudinal adjustment for a proton range during treating a tumor, and the continuous and adjustable proton beam is respectively transmitted to the fixed therapy room subsystem 11 and the rotating frame therapy subsystem 12 by the deflection dipole iron of the beam transport system. The cooperative control of the superconducting cyclotron system, the energy selection system, the beam transport system and the therapy head realize the transverse expansion of proton beam, and complete the conformally modulated intensity therapy for the tumor. The compact built-in ion source reduces the volume and the cost of the superconducting cyclotron; the compact floor space reduces structural costs and improves service performance; there is no high energy consumption and high heat dissipation caused by the constant temperature electromagnet; The invention can effectively solve the problems such as inaccurate tumor positioning in current tumor therapy, long therapy process, and poor postoperative quality of life of patients after surgery; the invention plays an extremely important role in promoting the precision, effectiveness and efficiency of tumor therapy for patients.

The above embodiments are only illustrative. All details of the invention are not described in detail in above embodiments, so these embodiments are not intended to limit the scope of the invention. Obviously, various modifications and changes may be made according to the contents of this specification. These embodiments are selected and described in this specification in order to better explain the principle and practical application of the invention, so that those skilled in the art can better understand and use the invention. The invention is limited only by the appended claims and full scope and equivalents thereof.

What is claimed is:

1. A proton therapy system based on a compact superconducting cyclotron, comprising:
    a superconducting cyclotron system;
    an energy selection system;
    a beam transport system;
    a fixed therapy room subsystem; and
    a rotating frame therapy subsystem;
    wherein the energy selection system is configured to adjust a fixed-energy proton beam extracted from a superconducting cyclotron of the superconducting cyclotron system into a continuous and adjustable proton beam of 70 MeV to 200 MeV, realizing a longitudinal adjustment for a proton range during treatment of a tumor, and the beam transport system is configured to respectively transmit the continuous and adjustable proton beam to the fixed therapy room subsystem and the rotating frame therapy subsystem;
    the beam transport system comprises a first 63-degree deflection dipole iron and a restriction slit to adjust an emittance of the continuous and adjustable proton beam; the beam transport system further comprises a second 63-degree deflection dipole iron and a first 30-degree deflection dipole iron to transmit the continuous and adjustable proton beam with required energy to therapy subsystems of two different tracks, respectively; the beam transport system further comprises a second 30-degree deflection dipole iron to transmit one track of the continuous and adjustable proton beam to the fixed therapy room subsystem, and the beam transport system further comprises a third 30-degree deflection dipole iron and a fourth 30-degree deflection dipole iron to transmit the other track of the continuous and adjustable proton beam to the rotating frame therapy subsystem; and the beam transport system further comprises a first 60-degree deflection dipole iron, a second 60-degree deflection dipole iron and a 90-degree deflection dipole iron to continuously transmit the other track of the continuous and adjustable proton beam to a rotating therapy head.

2. The proton therapy system of claim 1, wherein a section of the beam transport system between an outlet of the superconducting cyclotron and a first vacuum window of the fixed therapy room subsystem is in vaccum to transmit the continuous and adjustable proton beam; and the beam transport system further comprises a fixed therapy head to perform tumor radiotherapy by the continuous and adjustable proton beam; a section of the beam transport system between the outlet of the superconducting cyclotron and a second vacuum window of the rotating frame therapy subsystem is in vacuum to transmit the continuous and adjustable proton beam, and the beam transport system further comprises a rotating therapy head to perform the tumor radiotherapy by the continuous and adjustable proton beam;
    a first beam blocker is arranged at the outlet of the superconducting cyclotron; a second beam blocker and a third beam blocker are arranged in the fixed therapy room subsystem; the rotating frame therapy subsystem is provided with a fourth beam blocker and a fifth beam blocker.

3. The proton therapy system of claim 1, wherein the rotating frame therapy subsystem comprises a rotating frame, a rotating therapy head, a flat plate receiver, an imaging bulb tube, a flexible manipulator, a carbon fiber therapy bed, a positioning control device, a therapy information display system, and an imaging control device;
    the rotating frame has a cylinder crimping main body with variable diameters; a drive system of the rotating frame uses a single driven gear to match with dual driving gears; when the rotating frame receives a motion instruction, the motion instruction is transmitted to a position full-closed control system, which drives the dual driving gears to drive the single driven gear to achieve precise positioning of the rotating frame; the rotating therapy head and a CBCT device are fixedly connected with the rotating frame; the rotating frame uses a multi-directional detection method, and when the carbon fiber therapy bed collides with the rotating therapy head and the CBCT device during the rotation process of the rotating frame, a position encoder sends out an emergency signal, and the drive system of the rotating frame acts immediately to complete an emergency stop, thus ensuring the safe operation of the rotating therapy head and the CBCT device.

4. The proton therapy system of claim 3, wherein the rotating therapy head is configured to accurately radiate the energy in the beam transport system to the tumor of a patient by the control system; the imaging control device is configured to feed back tumor information of the patient to the therapy system in real time to adjust dose and position of the therapy in real time; the carbon fiber therapy bed achieves an ultra-low loss penetration of high energy rays to control a therapy process with maximum precision.

\* \* \* \* \*